(12) United States Patent
Trumm et al.

(10) Patent No.: US 10,337,953 B2
(45) Date of Patent: Jul. 2, 2019

(54) METHOD AND APPARATUS FOR DETERMINING SURFACE DATA AND/OR MEASUREMENT DATA RELATING TO A SURFACE OF AN AT LEAST PARTIALLY TRANSPARENT OBJECT

(71) Applicant: RODENSTOCK GMBH, München (DE)

(72) Inventors: Stephan Trumm, München (DE); Rainer Sessner, Roth (DE); Dietmar Uttenweiler, Icking (DE)

(73) Assignee: RODENSTOCK GMBH, München (DE)

( * ) Notice: Subject to any disclaimer, the term of this patent is extended or adjusted under 35 U.S.C. 154(b) by 13 days.

(21) Appl. No.: 15/555,300

(22) PCT Filed: Mar. 23, 2016

(86) PCT No.: PCT/EP2016/056367
§ 371 (c)(1),
(2) Date: Sep. 1, 2017

(87) PCT Pub. No.: WO2016/192869
PCT Pub. Date: Dec. 8, 2016

(65) Prior Publication Data
US 2018/0058977 A1    Mar. 1, 2018

(30) Foreign Application Priority Data

Jun. 3, 2015    (DE) .......................... 10 2015 108 839

(51) Int. Cl.
*G01M 11/02*    (2006.01)
*G01N 21/21*    (2006.01)

(52) U.S. Cl.
CPC ...... *G01M 11/0207* (2013.01); *G01M 11/025* (2013.01); *G01M 11/0264* (2013.01); *G01N 21/21* (2013.01)

(58) Field of Classification Search
CPC ........... G01M 11/0207; G01M 11/025; G01M 11/0264; G01N 21/21; G01B 9/00; G01B 11/0641; G02B 27/0012; G02B 27/28
(Continued)

(56) References Cited

U.S. PATENT DOCUMENTS

| 7,688,431 B1 | 3/2010 | Balch et al. |
| 2001/0001572 A1 | 5/2001 | Ikezawa et al. |

(Continued)

FOREIGN PATENT DOCUMENTS

| DE | 10 2011 078 833 A1 | 1/2013 |
| JP | 6-242410 A | 9/1994 |

(Continued)

OTHER PUBLICATIONS

English translation of Japanese Office Action for Japanese Application No. 2017-546833, dated Oct. 23, 2018.
(Continued)

*Primary Examiner* — Frank G Font
(74) *Attorney, Agent, or Firm* — Birch, Stewart, Kolasch & Birch, LLP

(57) ABSTRACT

A method and an apparatus for determining surface data and/or measurement data relating to a surface, for the quality control of an at least a partially transparent object, an ophthalmic lens, having an optically active first surface and an opposite optically active second surface. The method includes irradiating polarized light with an irradiation polarization from at least one illumination device onto an analysis area of the object to be examined, wherein, for the purpose of setting the irradiation polarization, the light is passed (Continued)

Figure 1:
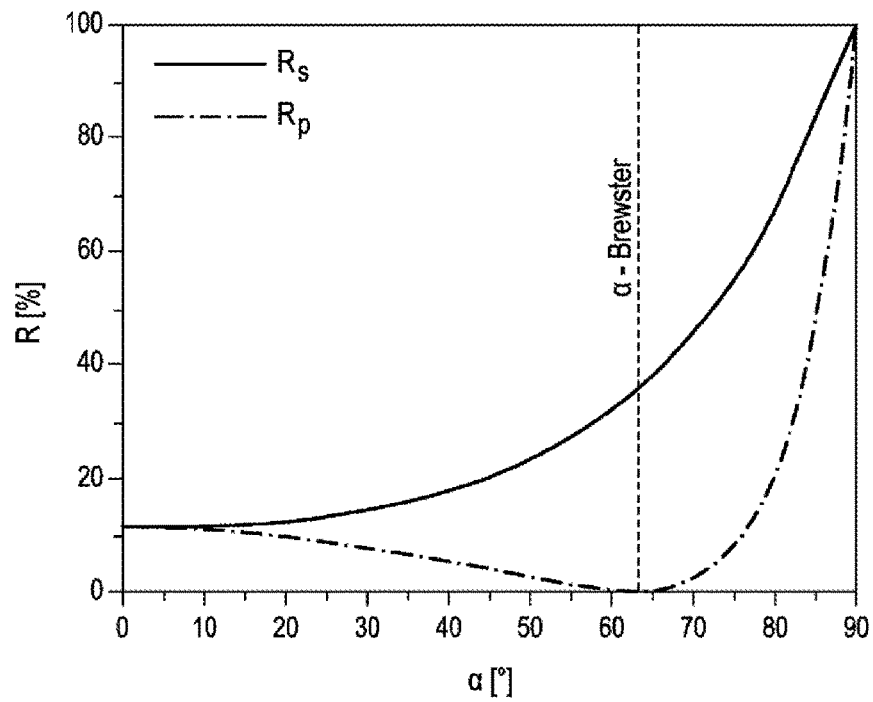

through a polarizer assigned to the illumination device or integrated in the latter, and receiving light which is reflected at the first and/or second surface and has an analysis polarization by use of at least one receiving device, wherein the light is passed through an analyzer assigned to the receiving device or integrated in the latter.

20 Claims, 6 Drawing Sheets

(58) Field of Classification Search
USPC .......... 359/369–371; 356/124, 127; 351/200, 351/205, 233
See application file for complete search history.

(56) References Cited

U.S. PATENT DOCUMENTS

| | | | |
|---|---|---|---|
| 2006/0250611 A1* | 11/2006 | Velidandla | G01B 11/303 356/237.2 |
| 2007/0146632 A1* | 6/2007 | Chipman | A61B 3/12 351/205 |
| 2009/0161114 A1 | 6/2009 | Yuan | |
| 2009/0323081 A1* | 12/2009 | Hirano | G01B 5/0004 356/601 |
| 2010/0268069 A1 | 10/2010 | Liang | |
| 2013/0250099 A1 | 9/2013 | Iijima et al. | |

FOREIGN PATENT DOCUMENTS

| | | |
|---|---|---|
| JP | 2007-240168 A | 9/2007 |
| JP | 2007-533977 A | 11/2007 |
| JP | 2010-518407 A | 5/2010 |
| JP | 2013-200257 A | 10/2013 |
| RU | 2107903 C1 | 3/1998 |
| WO | WO 2005/086582 A2 | 9/2005 |
| WO | WO 2008/098293 A1 | 8/2008 |
| WO | WO 2014/019806 A1 | 2/2014 |

OTHER PUBLICATIONS

International Preliminary Report on Patentability and Written Opinion of the International Searching Authority (Forms PCT/IB/338, PCT/IB/373, PCT/IB/326 and PCT/ISA/237), dated Dec. 14, 2017, for International Application No. PCT/EP2016/056367, with an English translation of the Written Opinion.
International Search Report for PCT/EP2016/056367 dated Jun. 23, 2016.

* cited by examiner

METHOD AND APPARATUS FOR DETERMINING SURFACE DATA AND/OR MEASUREMENT DATA RELATING TO A SURFACE OF AN AT LEAST PARTIALLY TRANSPARENT OBJECT

PRIOR ART

The invention relates to a method for determining surface data and/or measurement data relating to a surface of an at least partially transparent object, in particular a spectacle lens, and to a device for determining surface data and/or measurement data relating to a surface, and a computer program product for determining surface data and/or measurement data relating to a surface.

In recent years, free-form technology has entered the optical industry. In the area of spectacle lenses this involves, for example, individually optimised lenses. However, the possibility of producing free-form surfaces has also given rise to the need to measure optical surfaces quickly, reliably and non-destructively, over the entire surface. Thus surface data are determined for quality assurance. The surface data can for example comprise height data and/or gradient data and/or curvature data of the surfaces.

One approach involves the use of optical whole-surface measurement techniques for determining surface data. Because the surfaces of lenses do not scatter light, but rather reflect it, conventional methods fall short here. Instead techniques known as deflectometry (or reflectometry) are utilised. In this case, a pattern is irradiated onto a measurement object and the image of this pattern reflected on the measurement object is recorded.

Coordinates from the projection (e.g. pixel coordinates of a projector) are assigned to coordinates of the recording (e.g. pixel coordinates of a camera). If the geometry of the projector and camera are known, the reflective surface can be concluded.

A differentiation is made, in principle, between methods designated as "whole-surface" methods and methods which work with discrete patterns. In whole-surface methods, whole-surface patterns (usually different stripe patterns with sinusoidal intensity curves) are irradiated one after the other and each image point of the camera is individually evaluated. Methods using discrete structures are also known as Hartmann-type methods. In these methods, discrete objects (in the simplest case points) are irradiated onto the surface of the object, the position thereof in the image of the camera is determined by image processing and the coordinates thereof are evaluated.

During the analysis, ambiguities can arise in the light intensities reflected from transparent objects. In particular, a defined point in the illumination device can be mapped in different ways into one and the same pixel of the camera, because the optical path is the result of the position of the reflection and the orientation of the reflecting surface in space.

Different methods are known for resolving this ambiguity and for calculating surface data. The required methods are described in detail, for example in the following documents: D. Malacara, Optical Shop Testing, Wiley Interscience 1992; H. Gross, B. Dorband (author), H. Miller, Non Interferometric Wavefront Sensing, in Metrology of Optical Components and Systems, Chapter 47, Volume 5, Handbook of Optical Systems, (H. Gross (ed.)), Wiley-VCH, 2012; stereo deflectometry (DE 10 2004 020 419 B3); direction coded deflectometry (DE 1 00 14 964 C2); quality control of spectacle lenses (EP 2 799 832 A2).

However, in all these methods it is common that the irradiated pattern for transparent specimens is reflected both from the front surface and from the rear surface of the object to be measured. Both images overlap in the camera so that a clear evaluation is difficult.

EP 2 799 832 A2 describes a method for quality control of a spectacle lens, in which first the topography of an optically active surface of the spectacle lens is determined, then local actual values I[X,V] of an optical variable of the spectacle lens are calculated taking account of the determined topography, twenty local target values S[X,V] for the at least one optical variable of the spectacle lens are subsequently calculated considering the local deviations F[X,V] of the calculated local actual value I[X,V], then a quality measure Q is determined for the spectacle lens, in which the calculated local variations F[X,V] are analysed and then the determined quality measure Q is evaluated according to a quality rule.

DISCLOSURE OF THE INVENTION

The problem addressed by the invention is that of providing a method which allows, in particular for quality assurance, surface data and/or measurement data relating to a surface of transparent objects such as spectacle lenses to be easily and reliably determined.

The further problem addressed by the invention is that of providing a device which allows, in particular for quality assurance, surface data and/or measurement data relating to a surface of transparent objects such as spectacle lenses to be easily and reliably determined.

The problems are solved through the features of the independent claims. Advantageous embodiments and advantages of the invention arise from the further claims, the description and the drawings.

A method is proposed for determining surface data and/or measurement data relating to a surface, in particular for quality control, of an at least partially transparent object, in particular a spectacle lens, having an optically active first surface and an opposite optically active second surface, comprising the irradiation of polarised light having an irradiation polarisation of at least one illumination device, onto an analysis area of the object to be investigated, wherein, in order to set the irradiation polarisation, the light is guided through a polariser assigned to or integrated in the illumination device, and light reflected from the first and/or second surface, having an analysis polarisation, is received by means of at least one receiving device.

The light is guided through an analyser assigned to or integrated in the receiving device. The method further comprises the at least partial suppression of an undesirable light intensity reflected from the first or second surface and received by the receiving device by setting of the irradiation polarisation of the polariser and/or the analysis polarisation of the analyser, and measuring an intensity distribution or a wavefront of the light received having the analysis polarisation, in order to determine the surface data and/or the measurement data relating to the surface in the analysis area. Alternatively or in addition to the intensity distribution, a shape of the wavefront can also be measured, which wavefront arises from a point source or consists of parallel light and is irradiated as part of a pattern or is irradiated on the object instead of a pattern.

The surface data and/or measurement data may involve for example, depending on the application, height data and/or gradient data and/or curvature data of the surface.

According to an advantageous embodiment of the method according to the invention, a deviation of the determined surface data from target data for the surface data, and/or a deviation of the measurement data from the target data for the measurement data of the surface, can be determined where appropriate.

An analyser in this case represents a polariser that is used for analysis of the reflected light. The plane of incidence of the light is the plane which is spanned from the direction of propagation of the incident light and from the normal to the reflective surface. This plane also contains the direction of propagation of the reflected light.

The method described here also at least partially suppresses undesirable reflections during measurement of surface data and/or measurement data relating to a surface of at least partially transparent objects, and thus delivers reliable measurement results of the surface. In this way, information can also be obtained, using a measurement, relating to the first and second surface, typically the front surface and rear surface, of the object. A particular application of the method according to the invention involves quality control of spectacle lenses. In this case, polarised light is used for the method and the fact is utilised that the reflection and transmission coefficients for perpendicular and parallel polarised light depend on the respective angle of incidence, and generally differ. Linearly polarised light can change polarisation during reflection and refraction. This is due to the fact that usually for the component which lies parallel to the plane of incidence (p-polarised), different reflection or transmission coefficients apply than for the components which are perpendicular to the plane of incidence (s-polarised). If the intensity of the two components is affected differently, the direction of the polarisation of the resulting reflected and/or refracted radiation changes. In principle, reflection and transmission coefficients are only valid for specific angles of incidence. For the measurement, the angle of incidence is given by the arrangement of the object and illumination device.

Although the actual angle depends on the respective position of the object and the gradient of the surface at the corresponding point, these deviations can however be considered small in some configurations in comparison with the angle specified by the layout.

However, independent from this, it is true that in many cases a complete suppression of an undesirable reflection is not required, rather an attenuation is already sufficient. Thus even large deviations in the angle of incidence and reflection are not critical. An extreme or intermediate angle (e.g. a flat object) can then be used.

The method according to the invention comprises the provision of an at least partially transparent object (e.g. lenses or spectacle lenses), performing the recordings through irradiation of light onto the object and receiving reflected light from the object and the assignment of the irradiated pattern elements/intensities from the light reflected at the front and/or rear surfaces of the object. The method further comprises determining of surface data and/or measurement data of at least one of the surfaces of the object and where appropriate a comparison step. The latter can comprise a comparison of surface data with target data for the surface data, a comparison of measurement data (e.g. position on the illumination device) with target data for the measurement data, or the calculation of the deviation of the surface data from the target data for the surface data on the basis of the variation of the measurement data from the target data for the measurement data. The target data for the measurement data can for example be obtained as the result of ray-tracing calculations, from the target data for the surface data. In addition, the method can also comprise an evaluation of the deviation where necessary. The method can further comprise the performance of an overall quality evaluation from the determined local deviations. In general, it is sufficient for the method according to the invention, to assign a part of the reflection and/or the intensity of a part of the pixels, and to determine data for a part of the surface.

As known in the prior art and for example described in the documents of Malacara, Dörband listed in the introduction, and the documents listed in the introduction on stereo deflectometry, direction encoded deflectometry and spectacle lens quality control, the light intensities reflected at the front surface can be evaluated in an appropriate way directly, while, during the analysis of the light intensity reflected on the rear surface, refraction at the front surface, transmission through the object, reflection at the rear surface, transmission back through the object and refraction again at the front surface should be taken into account.

In principle, it is also conceivable to extend the method to interfaces within optical elements which consist of part elements having different refractive indices, such as for example achromatic lenses such as Hall and Dolland achromatics and Hasting triplets. In this case, the term "surface" includes not only the front and rear surface, but also the interfaces inside the optical element, for example between different materials.

Setting up the polarisation of the irradiated light by means of the selected position of the polariser of the illumination device, the possible change of the polarisation on reflection at a surface and the selection of a determined polarisation of the received light by means of the position of the analyser of the receiving device allows a targeted at least partial suppression or a targeted enhancement of individual reflexes. This allows, for example, reflexes from the front surfaces or the rear surfaces to be filtered out in a targeted manner.

According to an advantageous embodiment, the irradiation polarisation and/or the analysis polarisation can be selected such that, in the measured intensity distribution, the undesirable light intensity corresponds to the light received by the receiving device which is differently polarised to the analysis polarisation, and/or a desirable light intensity corresponds to the light received by the receiving device which is polarised in the same way as the analysis polarisation.

In this way, the irradiation polarisation and/or the analysis polarisation can be selected such that the detected proportion of the desirable light intensity, i.e. the light intensity which returns from reflection at one surface, is greater than the detected proportion of the undesirable light intensity, i.e. the light intensity which returns from reflection on the other surface and, in special cases, even such that the detected portion of the undesirable light intensity is completely suppressed. The use of differently orientated polarisations of the polariser and analyser, as well as the gradual adjustment of the polarisations of the polariser and analyser with respect to each other, allows targeted reflexes of the front surface and/or the rear surface of the object to be attenuated and thus to position the focal point for the evaluation of the reflexes on the front surface or the rear surface and to determine data relating to the surfaces from this.

In addition, the irradiation polarisation and/or the analysis polarisation are selected such that, in the measured intensity distribution, the undesirable light intensity corresponds to the light received by the receiving device which is polarised perpendicular to the analysis polarisation, and the desirable light intensity corresponds to the light received by the receiving device which is not polarised perpendicular to the analysis polarisation.

Here too, the irradiation polarisation and the analysis polarisation can be selected in particular such that the detected proportion of the desirable light intensity, i.e. the light intensity which returns from reflection at one surface, is greater than the detected proportion of the undesirable light intensity, i.e. the light intensity which returns from reflection at the other surface, and even such that the detected portion of the undesirable light intensity is completely suppressed.

The use of differently orientated polarisations of the polariser and analyser, as well as the gradual adjustment of the polarisations of the polariser and analyser with respect to each other, allows targeted reflexes of the front surface and/or the rear surface of the object to be attenuated, and thus to position the focal point for the evaluation of the reflection on the front surface or the rear surface and to determine data relating to the surfaces from this.

The angular position for suppression of the reflection on the front and/or rear surface is not necessarily different by 90°. In such cases, the reflection from the other surface is reduced, which is however not critical for the analysis of the light intensity. Further, for a plurality of polariser positions, the respective position of the analyser required for at least partial suppression of the reflexes of one surface, and the associated intensity of the not to be suppressed reflexes, are determined. The positions in which the remaining intensity of the reflexes which are not to be suppressed or the contrast between the two reflexes is maximised are then preferred.

According to an advantageous embodiment, the irradiation polarisation can be polarised perpendicular or parallel to a plane of incidence that is spanned by the light incident on the object and the light received by the receiving device. Perpendicular and/or parallel polarisations can preferably be used since here only one component occurs as a reflection and thus no rotation, but rather a suppression, of the reflection occurs.

According to an advantageous embodiment, the irradiation polarisation and the analysis polarisation can be differently aligned.

In particular, during use of an irradiation polarisation, which is polarised perpendicular or parallel with respect to a plane of incidence, a mutually orthogonal orientation of irradiation polarisation and analysis polarisation is particularly favourable.

According to an advantageous embodiment, a plurality of illumination devices can be used in parallel, the irradiation polarisations of which can also be orientated differently from one another, and/or a plurality of receiving devices can be used in parallel, the analysis polarisations of which can also be orientated differently from one another.

Since the reflection and transmission coefficients of the objects are dependent on the local gradient of the surface to be tested, the measurement range, i.e. size and local gradient of the surface can be extended, in that either a plurality of receiving devices and/or a plurality of illumination devices are used. This allows a larger surface of the object to be covered.

In this way too, objects within a given measurement volume having more strongly different surface gradients can be measured. This is due to the fact that the respective reflection and transmission coefficients depend on the angle of incidence and thus a greater range of gradients with similar angles of incidence and reflection can be covered by a plurality of receiving devices and/or a plurality of illumination devices.

According to an advantageous embodiment, the irradiated light can irradiate discrete pattern elements onto the first and second surfaces of the object. In this way, the determining of surface data and/or measurement data in the analysis area of one of the two surfaces of the object from the measured intensity distribution can comprise detecting the position of at least one reflected pattern element in the intensity distribution received by the receiving device, assigning the reflected pattern element to the surface on which the reflection occurs, and using the position of the pattern element on the illumination device and the position of the reflected pattern element in the measured intensity distribution, in order to determine surface data and/or measurement data.

It can be advantageous to work with apparatuses which generate individual beams and/or separable patterns, below also referred to as pattern elements. Depending on the method used, the generated radiation can be diffuse (e.g. conventional deflectometry methods) or directed (e.g. direction encoded deflectometry, methods with defined irradiated wavefronts). A diffuse radiation can be created, for example, using a display, a projection system (e.g. display in transmission, micro-mirror, slide, aperture, or (micro)lens arrangements) in combination with a scatter plate or individually and at least partially diffuse light sources (e.g. LEDs).

A directed radiation can be generated, for example, by such a projection system without scatter plate or by a display and/or a projection system with scatter plate and subsequent optics (e.g. f-theta-lens). The steps for assigning the reflections visible in recordings of said pattern elements to the front and/or rear surface can either be carried out before selection of the individual pattern elements at the pixel level or preferably after selection for each identified pattern element. The assignment at the pixel level can usefully be carried out in an analogue manner.

In general, after identification of the pattern elements, each pattern element is assigned a position in the recordings by means of the pixel coordinates of the receiving device, as well as a position in the illumination device by means of the pixel coordinates in the illumination device. In this way, on the basis of the known geometry of the measurement architecture, surface data and/or measurement data of the surface to be measured can be determined in a known manner.

In principle, a polariser position can be used in this method. Then, with an analyser position, reflexes at the front surface and at the rear surface or also at both surfaces can be used in order to assign the pattern elements.

Advantageously, two analyser positions can be used, in which the front surface reflex or reflexes, which originate from individual pattern elements, are determined by exclusion of the rear surface reflex or reflexes from a set and/or recording, which may contain reflections from both surfaces. Likewise, a determination of the rear surface reflexes is conceivable by means of exclusion of the front surface reflex or reflexes.

It is also conceivable to work with more than two analyser positions, in order to enable such a determination of the desirable reflex with simultaneous attenuation of the undesirable reflexes, and thus to enable an assignment of the desirable reflex to the pattern elements and from this to enable a determination of the surface data and/or measurement data relating to a surface. It is also conceivable to proceed in a similar manner with a plurality of polariser positions, in order to attain a still better differentiation between desirable and undesirable reflexes.

According to a preferred embodiment, during assigning of the at least one pattern element to the surface on which the reflection takes place, the light intensity of the respective reflected pattern element is compared with a threshold value that is specified or determined from the measured intensity distribution. In this way, advantageously only reflexes of pattern elements are selected for which the intensity exceeds a threshold value, in order to enable a secure assigning of the pattern elements.

According to an advantageous embodiment, during assigning of the at least one pattern element to the surface on which the reflection takes place, the polarisation of the respective reflected pattern element is at least approximately determined on the basis of the measured intensity distribution. Such an approach is appropriate, since in this way the assignment of the reflexes to the pattern element can be reliably determined. The polarisation of a reflex can then be advantageously determined by means of two measurements with mutually orthogonal positions of the analyser.

According to an advantageous embodiment, the irradiated light can irradiate planar or linear patterns, in particular lines, bars, for example with a constant or sinusoidal intensity distribution, or a continuous intensity distribution onto the first and second surface of the object. As described in the case of discrete pattern elements, diffuse or directed radiation can be used. The determining of the surface data and/or measurement data in the analysis area of one of the two surfaces of the object from the measured intensity distribution can comprise the determining of the light intensity produced by reflection at the at least one surface and received by the receiving device, for at least one point in the measured intensity distribution, the assigning of the point to the position from which the light originates on the illumination device, which by reflection at the surface is mapped into the point of the measured intensity distribution, and the use of the position of the point in the measured intensity distribution and the assigned position on the illumination device in order to determine the surface data and/or measurement data relating to a surface.

This method does not map individual separable pattern elements, but rather a whole-surface pattern. Therefore, in each pixel of a receiving device, the intensities of the point-shaped reflexes of the corresponding surface element of the front surface and the corresponding surface element of the rear surface interfere. Since, for the usually incoherent interference, the intensities are summed, the contributions of the front and rear surface are again separated for the analysis in each pixel.

Since the analysis utilises the intensity of the individual pixels, in each pixel of the receiving device the number of front surface reflexes and/or the proportion of the reflection from the rear surface is determined. The method relates to determining "recordings" which reflect the intensity of the front or rear surface reflexes. From these, the position of the illumination device imaged over the object can then be reconstructed in a known manner for each individual pixel of the receiving device. In this way, in a likewise known manner depending on the specified geometry of the measurement device, surface data and/or measurement data of the surface to be measured can be determined.

In order to increase the accuracy and/or reliability of the measurement, or in the case where separation of the intensities of the front-side and rear-side reflections using the above described method is not possible due to unsuitable geometries of the object (e.g. object geometry with greatly differing orientation of the object surface to the illumination direction), the following method can be carried out:

first recording with a first polariser position (index A in the following description of measurement variables) and a first analyser position (index 1), second recording with the first polariser position (index A) and a second analyser position (index 2), first recording with a second polariser position (index B) and a third analyser position (index 3), second recording with the second polariser position (index B) and a fourth analyser position (index 4), pixel by pixel calculation of the proportion of the light intensity resulting from front-side and rear-side reflection by solving a system of equations, as described below.

The front-side (index V) and rear-side reflexes (index R) map light from different sources (e.g. different pixels of a matt screen) and thus different original intensities E onto the same pixel of the receiving device, which detects the intensity D at that location. While the front-side reflex is reflected on the front side only (reflection coefficient $R^V$), for the rear-side reflex (effective reflection coefficient $R^R$), a first refraction (transmission coefficient of the refraction $B^{R1}$) at the front side, a first transmission (transmission coefficient $T^{R1}$) through the object, the reflection on the rear side of the object (reflection coefficient $R^1$), a second transmission back through the object (transmission coefficient $TR^2$) and finally a second refraction on exiting the object (transmission coefficient $BR^2$) take place.

This means that the polarisation directions denoted by A, B, 1 and 2 are not necessarily s- or p-polarised. Accordingly, the reflection coefficients depend in a known way on the components in the respective polarisation.

The following equation system applies to the four measurements $$D_A^1 = R_{A1}^V \times E_A^V + R_{A1}^R \times E_A^R$$

$$D_A^2 = R_{A2}^V \times E_A^V + R_{A2}^R \times E_A^R$$

$$D_B^3 = R_{B3}^V \times E_S^V + R_{B3}^R \times E_B^R$$

$$D_B^4 = R_{B4}^V \times E_S^V + R_{B4}^R \times E_{AB}^R$$

In order to determine the intensities of the front-side and rear-side reflexes, the system must first be solved for the unknowns $E_A^V$, $E_A^R$, $E_B^V$ and $E_B^R$.

If the coefficients R of the equation system are known from knowledge of geometry of the measurement system, the unknowns $E_A^V$, $E_A^R$, $E_B^V$ and $E_B^R$ can be calculated directly.

In this case, the same intensities are preferably selected on the illumination device for polarisation directions A and B, or intensities which differ only by known factors I $$\left( E^R = \frac{E_A^R}{I_A^R} = \frac{E_B^R}{I_B^R} \text{ and } E^V = \frac{E_A^V}{I_A^V} = \frac{E_B^V}{I_B^V} \right)$$

whereby the number of unknowns is halved and reduced to $E^R$ and $E^V$.

The attained degrees of freedom can be used to determine unknown coefficients or unknown parameters, on which the coefficients depend in an a-priori known manner.

If the analyser polarisations are selected such that the reflections of the front surface disappear (e.g. selection of s- and p-polarisation for the irradiation polarisations A and/or B and the analysis polarisations 2,4 and/or 1,3, then components $R_{A1}{}^V$ and $R_{B4}{}^V$ disappear), simplifying the equation system.

If the above simplifications are applied, one obtains $$D_S{}^1 = R_{S1}{}^R \times E^R$$

$$D_S{}^2 = R_{S2}{}^V \times E^R + R_{S2}{}^R \times E^R$$

$$D_P{}^3 = R_{P3}{}^V \times E^V + R_{P3}{}^R \times E^R$$

$$D_P{}^4 = R_{P2}{}^R \times E^R$$

According to an advantageous embodiment, during assignment of the position of the at least one point on the illumination device, the polarisation of each reflected point is at least approximately determined on the basis of the measured intensity distribution. Such an approach is appropriate, since in this way the assignment of the reflex to the pattern element can be reliably determined.

According to an advantageous embodiment, for an at least partial suppression or enhancement of light reflected at the first surface, the analysis polarisation can be determined by calculation. Thus the method comprises the breaking down of the irradiated polarised light into perpendicular and parallel polarised components in a plane of incidence. Then, the light intensity of the two components is multiplied by respective reflection coefficients resulting from an angle of incidence and a refractive index of a material of the object and the thus obtained components of the reflected light are combined. Then the polarisation direction of the reflected light is determined and the analysis polarisation of the analyser is set at least approximately perpendicular or at least approximately parallel to the polarisation direction of the reflected light. The at least partial suppression of the reflex of the front surface serves, according to the invention, to clearly emphasise or isolate the rear-side reflex. The determination of the orientation of the polarisation axis is conceptually simpler for the front surface reflex than for the rear surface reflex, because only one reflection needs to be considered here. In general, at least partial suppression or enhancement of the reflex of the front surface can be carried out with each position of the polariser. The position of the analyser is accordingly adapted.

According to an advantageous embodiment, for an at least partial suppression or enhancement of light reflected at the second surface, the analysis polarisation is determined by calculation. The method comprises the breaking down of the irradiated polarised light into perpendicular and parallel components in a first plane of incidence of the light, corresponding to the plane of incidence of the refraction at the first surface, and the subsequent multiplying of the light intensity of both components with respective transmission coefficients resulting from a first angle of incidence and the refractive index of the material of the object.

The method further comprises the conversion of these components into perpendicular and parallel polarised components in a second plane of incidence, which corresponds to the plane of incidence of the reflection at the second surface, and the subsequent multiplying of the light intensity of both components by a respective reflection coefficient, which results from a second angle of incidence given by the refraction at the first surface and reflection at the second surface and from the refractive index of the material of the object and/or of a holder.

These components are then converted into perpendicular and parallel polarised components in a third plane of incidence, which corresponds to a plane of incidence of the second refraction at the first surface, and the light intensity of both components are multiplied by a respective second transmission coefficient, resulting from a third angle of incidence given by the reflection at the second surface and the first surface and the refractive index of the material of the object.

The thus obtained components of the transmitted light are combined and the polarisation direction of the light refracted through the first surface for the second time is determined, and the analysis polarisation of the analyser is set at least approximately perpendicular or at least approximately parallel to the polarisation direction of the light refracted for the second time through the first surface.

The at least partial suppression of the reflex from the rear surface serves, according to the invention, to clearly emphasise or isolate the front-side reflex. The determination of the rotation of the polarisation axis is conceptually more complex for the rear surface reflex than for the front surface reflex, because in this case two refractions, two transmissions and a reflection need to be considered. In general, here too at least partial suppression or enhancement of the rear surface reflex can be carried out with each position of the polariser. The position of the analyser is accordingly adapted.

The angles and planes of incidence discussed in the two preceding paragraphs do not however necessarily need to correspond to the angles or planes of incidence actually occurring at the object. Rather, it is sufficient in many cases to consider angles or planes of incidence which lie in the range (for example in the middle or at boundary) of angles to be expected for an object or for a distribution of objects.

According to an advantageous embodiment, for an at least partial suppression of the light intensity of the light reflected at the first or second surface, the position of the polariser and/or analyser can empirically be determined. The method in this case comprises the setting of an arbitrary position of the polariser and an arbitrary position of the analyser.

Next, the intensity distributions of the light reflected at the first and second surface are measured, and the contrast between the light reflected at the first surface and the light reflected at the second surface is evaluated. After this, the positions of the polariser and/or analyser are iteratively adjusted until a predetermined or a maximum contrast to be achieved between the light reflected at the first surface and the light reflected at the second surface is attained, or a limiting value for the intensity of the undesirable light is reached or has a value below the limiting value. In addition to the mathematical determination of the polariser and analyser positions, an empirical procedure is also possible in order to minimise an undesirable reflex.

In a further aspect, the invention relates to an apparatus for determining surface data and/or measurement data relating to a surface of an at least partially transparent object, in particular a spectacle lens, using the above-described method. The apparatus comprises at least one illumination device comprising a polariser having an irradiation polarisation, arranged on an optical axis after or as part of the illumination device, at least one receiving device comprising an analyser having an analysis polarisation, arranged on an optical axis before or as part of the receiving device, and a holder for the object.

Discrete pattern elements and/or planar patterns can be irradiated by the illumination device through the polariser onto the object and can be detected by the receiving device through the analyser.

The illumination device comprises a pattern generator, which can comprise for example a display, a projection system, individual light sources or a combination of projection system with scatter plate. Depending on the method used, the generated radiation can be diffuse (e.g. conventional deflectometry methods) or directed (e.g. direction encoded deflectometry, methods with defined irradiated wavefronts).

A diffuse radiation can be generated, for example, from a display, a projection system (e.g. display in transmission, micro-mirror, slide, aperture or (micro)lens arrangements) in combination with a scatter plate or individual and at least partially diffuse light sources (e.g. LEDs). A directed radiation can be generated, for example, through such a projection system without scatter plate or through a display and/or a projection system with scatter plate and subsequent optics (e.g. f-theta-lens).

The receiving device comprises for example a camera, which is irradiated by the illumination device and captures the light reflected on the object. According to the invention, a polarising element is inserted both between illumination device and object, as well as between object and receiving device, provided that one or both of these polarising elements are not already part of the illumination device or the receiving device.

One or both of these polarising elements are rotatably mounted for example on the optical axis, so that different positions of the polarisation plane can be set.

Since the reflection and transmission coefficients of the objects are dependent on the local gradient of the surface to be tested, the measurement range, i.e. size and local gradient of the surface can be extended, in that either a plurality of receiving devices and/or a plurality of illumination devices are used. This allows a larger surface of the object to be covered.

In this way too, objects within a given measurement volume having more strongly different surface gradients can be measured. This is due to the fact that the respective reflection and transmission coefficients depend on the angle of incidence and thus a greater range of gradients with similar angles of incidence and reflection can be covered by a plurality of receiving devices and/or a plurality of illumination devices.

According to a particularly advantageous embodiment, discrete pattern elements and/or planar or linear patterns of the illumination device can be irradiated through the polariser onto the object and can be received by the receiving device through the analyser.

Alternatively, a wavefront (for example light from a point source or consisting of parallel light) can also be irradiated onto the object, wherein the wavefront can also additionally be superimposed on a pattern. The wavefront is reflected at the object (front and rear sides) and can then be analysed. Thus according to an advantageous embodiment, the illumination device with the polariser can irradiate radiation with a predetermined irradiation polarisation onto the object and the receiving device with the analyser can receive the wavefront of polarisation components determined by the analyser.

In this case, the irradiated radiation comprises a predetermined, in particular planar or spherical-shaped, wavefront and the receiving device can analyse the shape of the wavefront and thus operate according to the Hartmann principle (aperture plate and receiving unit), Shack-Hartmann principle ((micro-)lens array and receiving unit), the Moiré principle or by interferometry. In this case too, the reflexes from the front side and rear side can be separated according to the invention using a polariser in front of the object and an analyser after the object.

According to an advantageous embodiment, the apparatus can comprise a data processing device for analysing the light radiation received by means of the receiving device. The data processing device thus controls an analysis of the reflected light radiation received by the receiving device. This or another data processing device can also be connected to the illumination device and control the pattern generation of the illumination device. The illumination can be flexible or fixed.

A further aspect of the invention relates to a computer program product for determining surface data and/or measurement data relating to a surface of at least partially transparent object, particular a spectacle lens. The computer program product comprises a computer readable storage medium, which contains a program code that is configured to execute a method as described above, if the program code is executed on a data processing device.

DRAWINGS

Further advantages arise from the following description of the drawings. The drawings illustrate exemplary embodiments of the invention. The drawings, the description and the claims contain many features in combination. A person skilled in the art will also usefully consider these individually and combine them into meaningful further combinations.

Figure 2:
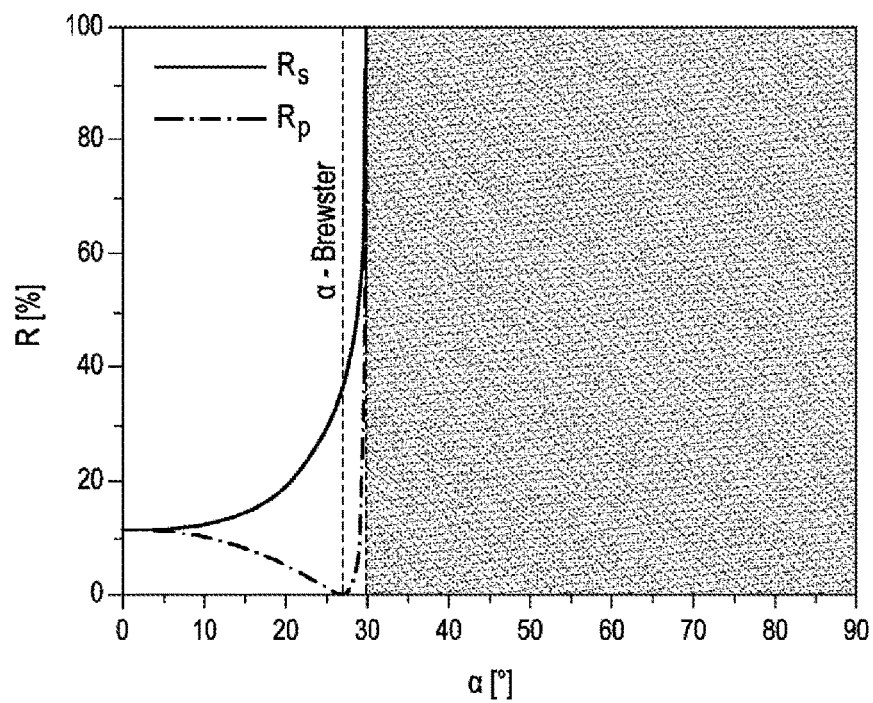
Figure 3:
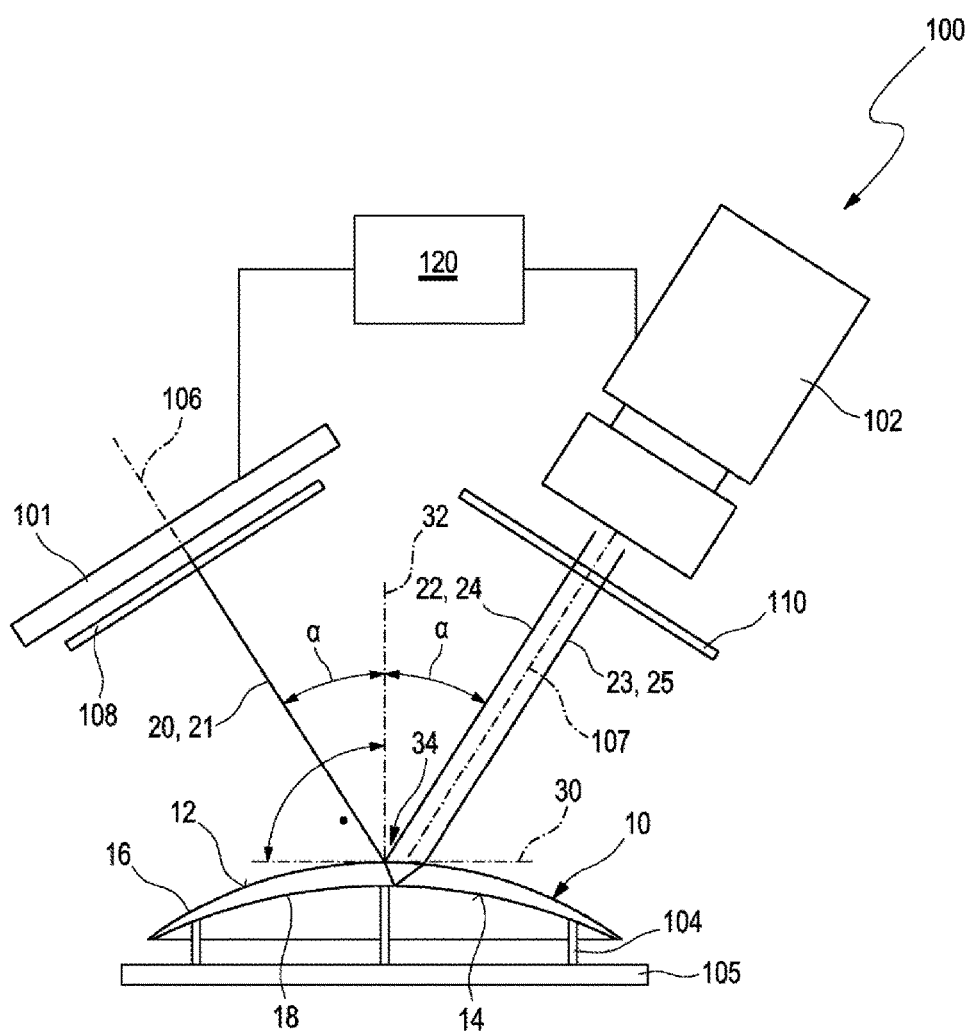
Figure 4:
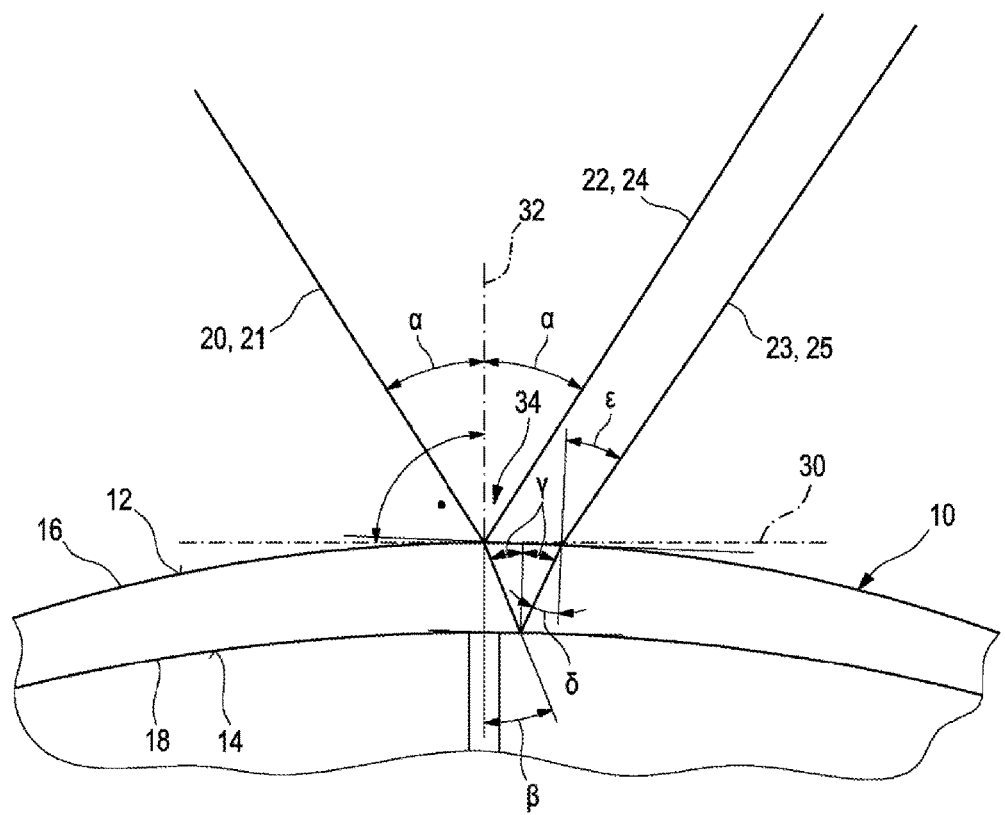
Figure 5:
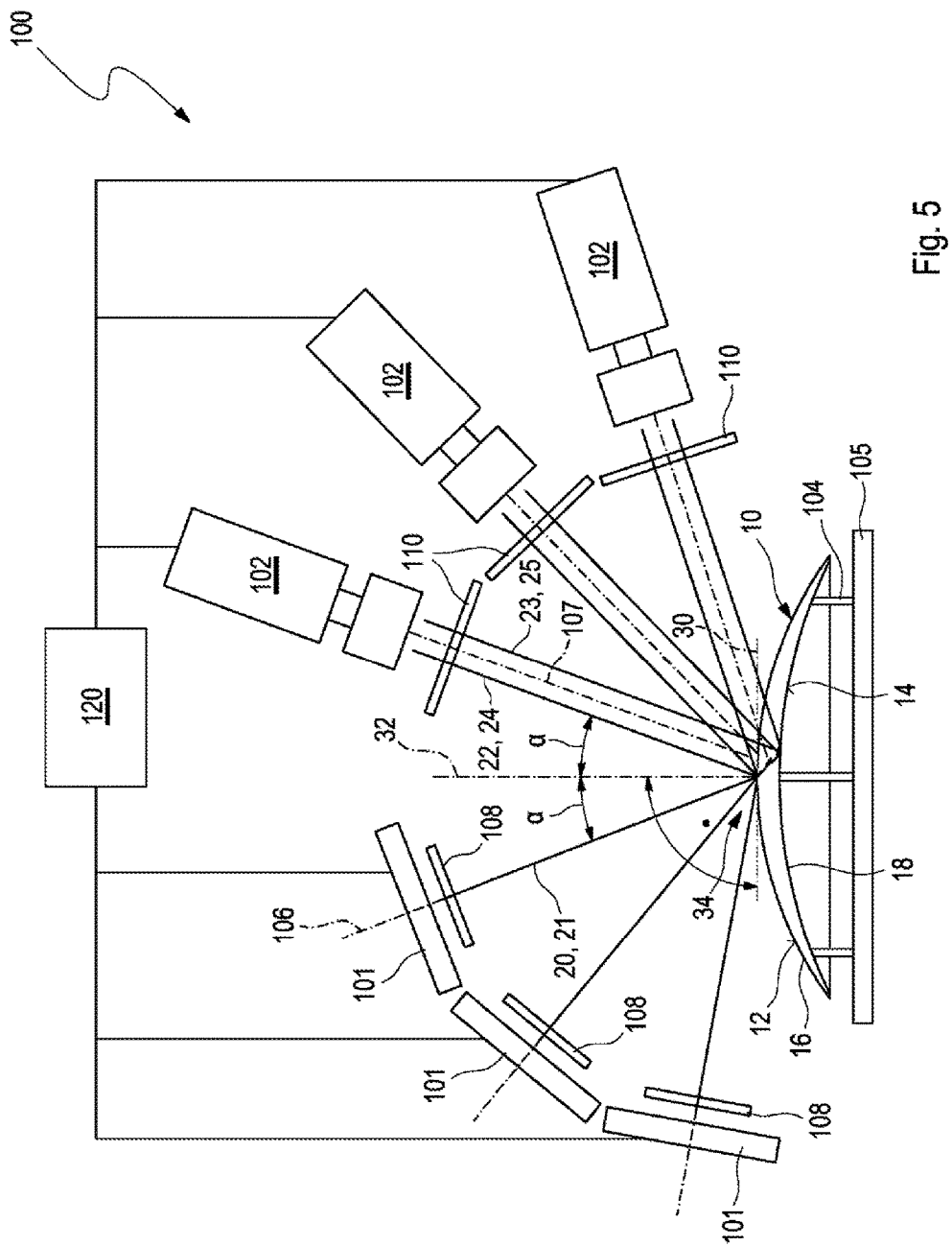
Figure 6:
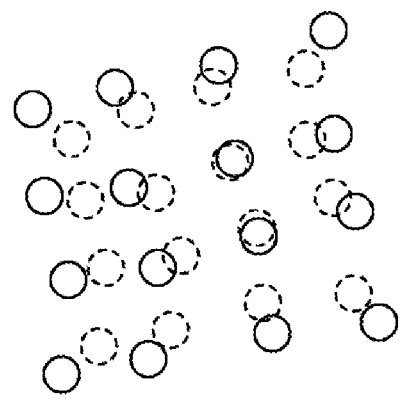
Figure 7:
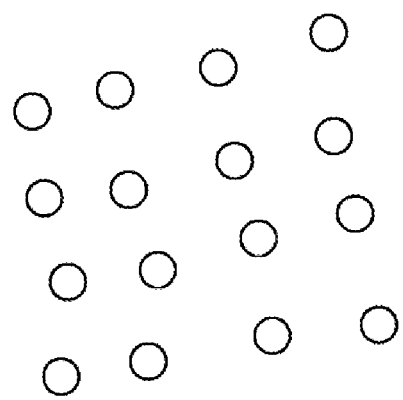
Figure 8:
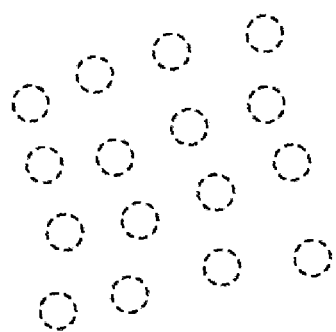
Figure 9:
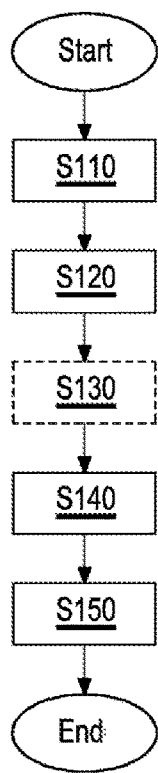
Figure 10:
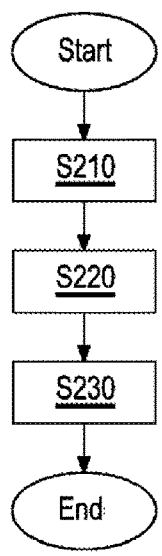
Figure 11:
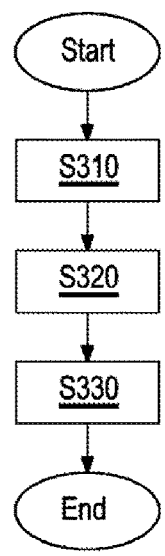
Figure 12:
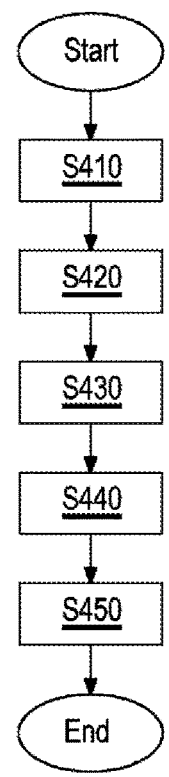

The drawings show, by way of example:

FIG. 1, reflection coefficients for reflection at a front surface of an object, for light polarised perpendicular and parallel to the plane of incidence;

FIG. 2, reflection coefficients for reflection at a rear surface of the object from FIG. 1, for light polarised perpendicular and parallel to the plane of incidence;

FIG. 3, a schematic representation of an apparatus for determining surface data and/or measurement data relating to a surface of an object according to an exemplary embodiment of the invention, comprising an illumination device and a receiving device;

FIG. 4, a definition of the angles of incidence and reflection of light rays reflected at the first and second surface of the object;

FIG. 5, a schematic representation of an apparatus for determining surface data and/or measurement data relating to a surface of an object according to a further exemplary embodiment of the invention with a plurality of illumination devices and a plurality of receiving devices;

FIG. 6, a schematic representation of a recording of the reflection of discrete pattern elements reflected from the front and rear surface of a spectacle lens, using an apparatus and a method according to an exemplary embodiment of the invention;

FIG. 7, a schematic representation of the recording of the reflection of the discrete pattern elements of FIG. 6, wherein through an analyser position orthogonal to the analyser position in FIG. 6, the front surface reflex is suppressed;

FIG. 8, a schematic representation of the recording of the reflection of the discrete pattern elements of FIG. 6, wherein through an analyser position different from the analyser positions in FIGS. 6 and 7, the rear surface reflex is suppressed;

FIG. 9, a flow diagram of a method for determining surface data and/or measurement data relating to a surface of an at least partially transparent object according to an exemplary embodiment of the invention;

FIG. 10, a flow diagram of a method for determining surface data and/or measurement data relating to a surface of an at least partially transparent object using discrete pattern elements, according to a further exemplary embodiment of the invention;

FIG. 11, a flow diagram of a method for determining surface data and/or measurement data relating to a surface of an at least partially transparent object using planar patterns, according to a further exemplary embodiment of the invention; and FIG. 12, a flow diagram for a further exemplary embodiment of the method according to the invention, in which the measurements are carried out using two analyser positions.

EMBODIMENTS OF THE INVENTION

In the figures, similar or similarly-acting components are marked with the same reference signs. The figures show examples only and are not to be understood as limiting.

FIG. 1 shows reflection coefficients for reflection at a front surface of a transparent object in the case of light polarised perpendicular ($R_s$) and parallel ($R_P$) to the plane of incidence, as a function of the angle of incidence α. Linearly polarised light can change its polarisation during reflection and refraction. This is due to the fact that usually, for the component which lies parallel to the plane of incidence (p), different reflection or transmission coefficients apply than for the components which are perpendicular to the plane of incidence (s). If the intensity of the two components is affected differently, the direction of the resulting reflected and/or refracted radiation changes. FIG. 1 shows the reflection coefficients for reflection at the front surface for an object made from a material having a refractive index of 2.0. The transmission coefficients complement the corresponding reflection coefficients to a total of 100%. Also illustrated is the Brewster angle, at which reflection of parallel orientated light is extinguished.

FIG. 2 shows the corresponding reflection coefficients for reflection at a rear surface of the object of FIG. 1 for light polarised perpendicular ($R_s$) and parallel ($R_p$) to the plane of incidence, as a function of the angle of incidence α. The region of total reflection at the rear surface of the object begins already at an angle of incidence of approximately 30°. The transmission coefficients complement the corresponding reflection coefficients to a total of 100%. Also illustrated is the Brewster angle, at which reflection of parallel orientated light is extinguished.

FIG. 3 shows a schematic representation of an apparatus 100 for determining surface data 16, 18 and/or measurement data relating to a surface 12, 14 of an object 10, in particular a spectacle lens, according to an exemplary embodiment of the invention, comprising an illumination device 101 and a receiving device 102. The apparatus 100 comprises the illumination device 101 comprising a polariser 108 having an irradiation polarisation, arranged after the illumination device 101 on an optical axis 106, the receiving device 102 comprising an analyser 110 having an analysing polarisation, arranged before the receiving device 102 on an optical axis 107, and a holder 104 for the object 10. In the method according to the invention, beams of light having discreet pattern elements or planar patterns and/or wavefronts 21 are irradiated from the illumination device 101 through the polariser 108 onto the object 10 and received by the receiving device 102 through the analyser 110. The apparatus further comprises a data processing device 120 for controlling the illumination device 101 and for analysis of the reflected light radiation received by the receiving device 102. The data processing device 120 controls the pattern generation of the illumination device 101 and analyses the reflected light radiation received by the receiving device 102.

The object 10 in the form of a spectacle lens comprises a first surface 12 (in this case the front surface of the spectacle lens) having corresponding surface data 16, such as height data, gradient data and curvature data, as well as a second surface 14 (in this case the rear surface of the spectacle lens) having corresponding surface data 18. The object 10 lies with the second surface 14 thereof on the holder 104, which is advantageously constructed as a tripod, in order to provide a stable and unambiguous mounting. The holder 104 is in turn arranged on a support 105. The irradiated light is incident with a specified intensity distribution 20 or wavefront 21 at an angle α with respect to the normal 32 to a tangential surface 30 on the front surface 12 of the object 10. The light is partially reflected at the front surface 12. The intensity distribution 22 or wavefront 24 of the light reflected at the front surface 12 is measured by the receiving device 102 through the analyser 110. The part of the incident light which is not directly reflected penetrates as transmission into the object 10. A part of the transmitted light is reflected at the rear surface 14, passes through the object 10 again, a part of this light is refracted at the front surface 12 and can then likewise be measured by the receiving device 102 in the intensity distribution 23 or wavefront 25.

FIG. 4 shows a definition of the angles of incidence and reflection or diffraction α, β, γ, δ, ε of light radiation reflected at the first surface 12 and the second surface 14 of the object 10. The angle α defines the angles of incidence and reflection of the radiation reflected at the first surface 12, which is measured as an intensity distribution 22 or wavefront 24. The angle β defines the angle of refraction which corresponds to the refraction of the incident radiation that entered the object at the first surface 12. The angle γ defines the angle of incidence and reflection, which arises through refraction at the first surface 12 and reflection at the second surface 14. The angles δ and ε define the angle of incidence and refraction, which result through the refraction of the radiation reflected at the second surface 14 at the first surface 12, which after leaving is measured as intensity distribution 23 or wavefront 25.

FIG. 5 shows a schematic representation of an apparatus 100 for determining surface data 16, 18 and/or measurement data relating to a surface of an object 10 according to a further exemplary embodiment of the invention with a plurality of illumination devices 101 and a plurality of receiving devices 102. This allows a larger surface of the object 10 to be covered. In this way too, objects within a given measurement volume having more strongly different surface gradients can be measured. This is due to the fact that the respective reflection and transmission coefficients depend on the angle of incidence and thus a greater range of gradients with similar angles of incidence and reflection can be covered by a plurality of receiving devices and/or a plurality of illumination devices.

FIG. 6 shows a schematic representation of a recording of the reflection of a pattern consisting of discrete pattern elements 16 reflected from the front surface 12 and rear surface 14 of a spectacle lens, using an apparatus 100 as represented in FIG. 3, and a method according to an exemplary embodiment of the invention. The measurement object (plastic lenses) is irradiated with an LED illumination, which represents the illumination device 100 and a pattern irradiated as four rows of four pattern elements. The image was taken by an industrial camera. The irradiated light was polarised by a piece of a film made from long chain polymers. A further piece of this film was used as the analyser in front of the receiving device. The polarisation direction of the analyser is thus perpendicular to the polarisation direction of the analyser that was used for taking the image shown in FIG. 7. The polarisation direction of the polariser by contrast, corresponds to the polarisation direction of the polariser that was used for taking the image shown in FIG. 7.

In comparison to this, FIG. 7 shows a recording of the reflection of the discrete pattern elements from FIG. 6, wherein the position of the polariser has been predetermined and the position of the analyser has been selected such that the front surface reflex is suppressed. Only the reflex from the rear side of the spectacle lens is visible.

FIG. 8 shows a further schematic representation of the recording of the reflection of the discrete pattern elements from FIG. 6, wherein, by means of a different analyser position to the analyser positions shown in FIGS. 6 and 7, the rear surface reflex is suppressed.

FIG. 9 represents a flow diagram of the method for determining surface data 16, 18 and/or measurement data relating to a surface 12, 14 of an at least partially transparent object 10, comprising an optically active first surface 12 and an opposite optically active second surface 14, in particular of a spectacle glass, according to an exemplary embodiment of the invention. The reference signs relate to the representation in FIG. 3. In step S110, polarised light, having an irradiation polarisation, from at least one illumination device 101 is irradiated onto an analysis area 34 of the object 10 to be investigated, wherein in order to set the irradiation polarisation, the light of the illumination device 101 is guided through a polariser 108. In step S120, light that is reflected at the first and/or second surface 12, 14 and having an analysis polarisation is received by means of at least one receiving device 102, wherein the light is passed through an analyser 110 assigned to the receiving device 102. Step S130 includes the at least partial suppressing of an undesirable light intensity reflected by the first or second surface 12, 14 and received by the receiving device 102, by setting the radiation polarisation of the polariser 108 and/or the analysis polarisation of the analyser 110. Alternatively, the polariser 108 and analyser 110 can already be set, before the beginning of the measurement, to appropriate, already known, positions for suppressing the undesirable light intensity. In step S140, where appropriate, after successful at least partial suppression of the undesirable light intensity in step S130, an intensity distribution 22, 23 of a light intensity reflected from the second or first surface 14, 12 and received by the receiving device 102 is measured over the analysis area 34, in order to detect surface data 16, 18 in the analysis area 34, while in step S150 said data is used to determine a deviation of the detected surface data 16, 18 in the analysis area 34 from target data in the analysis area 34.

The irradiation polarisation and the analysis polarisation are selected such that in the measured intensity distribution 22, 23 the undesirable light intensity corresponds to the light received by the receiving device 102, which is differently polarised to the analysis polarisation. Further, the irradiation polarisation and the analysis polarisation are selected appropriately such that the desirable light intensity corresponds to the light received by the receiving device 102, which is polarised in the same way as the analysis polarisation, wherein the desirable light intensity is greater than the undesirable light intensity. The irradiation polarisation and the analysis polarisation can advantageously be orientated differently to one another, in particular orthogonally orientated. Advantageously, the radiation polarisation is polarised perpendicular or parallel to a plane of incidence that is spanned by the light incident on the object 10 and the light received by the receiving device 102. In particular, in this case, the irradiation and analysis polarisation are advantageously arranged orthogonal to one another. A plurality of illumination devices 101 and/or a plurality of receiving devices 102 can be used in parallel, in order for example to cover larger analysis areas 34 of the object 10.

For an at least partial suppression of the light reflected at the first surface 12, i.e. the front surface of the object 10 (see FIG. 4), the analysis polarisation can be mathematically determined. For this purpose the irradiated polarised light is broken down into perpendicular and parallel polarised components in the plane of incidence. The light intensity of both components is then multiplied by respective reflection coefficients resulting from a first angle of incidence α and a refractive index of the material of the object 10. The components of the reflected light obtained in this way are combined and used to determine the polarisation direction of the reflected light. The analysis polarisation of the analyser 110 can be set at least approximately perpendicular to the polarisation direction of the reflected light.

For an at least partial suppression of the light reflected at the second surface 14, i.e. the rear surface of the object 10 (see FIG. 4), the analysis polarisation can likewise be mathematically determined. For this purpose the irradiated polarised light is broken down into perpendicular and parallel polarised components in a first plane of incidence of the light, corresponding to the plane of incidence of the refraction at the first surface 12, and the light intensity of both components is multiplied by respective transmission coefficients resulting from a first angle of incidence α and from the refractive index of the material of the object 10.

These components are transformed into perpendicular and parallel polarised components in a second plane of incidence, which corresponds to the plane of incidence of the reflection at the second surface 14, and from this the light intensity of the two components is multiplied by a respective reflection coefficient which result from the angle of incidence γ given by the refraction at the first surface 12 and at the second surface 14 and from the refractive index of the material of the object 10 and/or of a holder 104. These components are then transformed into perpendicular and parallel polarised components in a third plane of incidence, which corresponds to the plane of incidence of the second refraction at the first surface 12, and the light intensity of the two components is multiplied respectively by second transmission coefficients, resulting from an angle of incidence δ given by the reflection at the second surface 14 and the first surface 14 and the refractive index of the material of the object 10. Then, the thus obtained components of the refracted light are combined, the polarisation direction of the light refracted through the first surface 12 for the second time is determined, and therefore the analysis polarisation of the analyser 110 is set at least approximately perpendicular or at least approximately parallel to the polarisation direction of the light transmitted for the second time through the first surface 12.

Alternatively the light intensity of light reflected at the first or second surface 12, 14 is at least partially suppressed, by empirically determining the position of the polariser 108 and/or analyser 110. In this case, a random position of the polariser 108 and a random position of the analyser 110 are set, and the intensity distributions 22, 23 of the light reflected at the first and at the second surface 12, 14 is measured. The contrast between the light reflected at the first surface 12 and the light reflected at the second surface 14 is measured. After this, the positions of the polariser 108 and/or analyser 110 are iteratively adjusted, until a predetermined contrast between the light reflected at the first surface 12 and the light reflected at the second surface 14 is attained, or a limiting value for the intensity of the undesirable light is reached or has a value below the limiting value.

FIG. 10 shows a flow diagram of the method for determining surface data 16, 18 and/or measurement data relating to a surface 12, 14 of an at least partially transparent object 10 using discrete pattern elements, according to an exemplary embodiment of the invention. The irradiated light radiates discrete pattern elements onto the first and second surfaces 12, 14 of the object 10. In step S210, the position of at least one reflected pattern element in the intensity distribution 22, 23 received by the receiving device 102 is detected, while in step S220 the reflected pattern element is assigned to the surface 12, 14 at which the reflection takes place. In step S230, the position of the pattern element on the illumination device 101 and the position of the reflected pattern element in the measured intensity distribution 22, 23 are used in order to determine surface data 16, 18 relating to one of the surfaces 12, 14. During assigning of the at least one pattern element to the surface 12 or 14 on which the reflection takes place, the light intensity of the respective reflected pattern element can usefully be compared with a threshold value that is predetermined or determined from the measured intensity distribution 22, 23. During assigning of the at least one pattern element to the surface 12, 14 on which the reflection takes place, the polarisation of the respective reflected pattern element can be at least approximately determined on the basis of the measured intensity distribution 22, 23. The polarisation of a reflex can then be advantageously determined by means of two measurements with mutually orthogonal positions of the analyser 108.

FIG. 11 shows a flow diagram of the method for determining surface data 16, 18 and/or measurement data relating to a surface 12, 14 of an at least partially transparent object 10 using planar patterns, according to a further exemplary embodiment of the invention. The irradiated light radiates planar patterns, in particular lines or bars, for example with constant or sinusoidal intensity distributions, or a continuous intensity distribution, onto the first and second surfaces 12, 14 of the object 10. In step S310, the light intensity, that is created by reflection at the least one surface 12, 14 and received by the receiving device 102, is detected for at least one point in the measured intensity distribution 22, 23, while in step S320 the position on the illumination device 101 from which the light originates, which is mapped by reflection at the surface 12, 14 into the point of the measured intensity distribution 22, 23, is assigned to the corresponding point. In step S330, the position of the point in the measured intensity distribution 22, 23 and the assigned position on the illumination device 101 are used to determine the surface data of the assigned surface 12, 14. During assignment of the position of the at least one point on the illumination device 101, the polarisation of each reflected point can usefully be at least approximately determined on the basis of the measured intensity distribution 22, 23.

FIG. 12 further shows a flow diagram for an exemplary embodiment of the method according to the invention, in which the measurements are carried out using two analyser positions. Such measurements can the performed for example using discrete pattern elements. The irradiated light radiates discrete pattern elements onto the first and second surfaces 12, 14 of the object 10. In step S410 a first measurement using a position of analyser 108 and polariser 110 are recorded in such a way that the reflexes of the front surface 12 of the object 10 is attenuated. Then, in step S420, pattern elements are selected in the first image recording and the pattern elements which have an intensity exceeding a first threshold value are assigned to the set of rear-surface measurement reflexes. This set corresponds to the set of pattern elements schematically represented in FIG. 7. In step S430 a second measurement is carried out after rotation of the polarisation plane of the analyser 110, preferably through 90° or according to an angle previously determined according to the invention. In step S440, pattern elements in the second image recording are selected and the pattern elements which have an intensity exceeding a second threshold value are assigned to the set of all measurement reflexes. This set corresponds to the set of all pattern elements schematically represented in FIG. 6. In step S450, the elements of the set of rear-surface measurement reflexes are removed from the set of all measurement reflexes and the remaining elements are assigned to the front surface. This set corresponds to the set of pattern elements schematically represented in FIG. 8. In this way, the front-surface reflexes can be determined by rejecting the rear-surface reflexes. This method is particularly suitable if a suppression of the rear-side reflexes is difficult due to the geometry or material properties of the object 10.

The invention claimed is:

1. A method for determining data relating to a surface having an optically active first surface and an opposite optically active second surface, comprising:
   irradiating polarized light with an irradiation polarization from at least one illumination device onto an analysis area of the object to be examined, wherein, for the purpose of setting the irradiation polarization, the light is passed through a polarizer assigned to the illumination device or integrated in the illumination device,
   receiving light that is reflected at the first or second surface and has an analysis polarization by at least one receiving device, wherein the light is passed through an analyzer assigned to the receiving device or integrated in the receiving device,
   at least partially suppressing an undesirable light intensity reflected by the first or second surface and received by the receiving device through setting of the irradiation polarization of the polarizer or the analysis polarization of the analyzer,
   measuring an intensity distribution or a wavefront of the light received with the analysis polarization, in order to determine data relating to the surface in the analysis area.

2. The method according to claim 1, wherein, in the analysis area, a deviation of the data relating to the surface from a target data is determined.

3. The method according to claim 1, wherein the irradiation polarization and/or the analysis polarization is selected such that, in the measured intensity distribution, the undesirable light intensity corresponds to the light received by the receiving device that is polarized differently to the analysis polarization, or a desirable light intensity corresponds to the light received by the receiving device that is polarized in a same way as the analysis polarization, wherein a detected proportion of the desirable light intensity is greater than the detected proportion of the undesirable light intensity.

4. The method according to claim 1, wherein the irradiation polarization is polarized perpendicular or parallel to a plane of incidence that is spanned by the light irradiated on the object and the light received by the receiving device.

5. The method according to claim 1, wherein the irradiation polarization and the analysis polarization are differently orientated to one another.

6. The method according to claim 1, wherein the at least one illumination device comprises a plurality of illumination devices, and
wherein the plurality of illumination devices are used in parallel.

7. The method according to claim 1, wherein the irradiated light irradiates discrete pattern elements onto the first and second surface of the object and wherein determining of the data relating to the surface in the analysis area of one of the two surfaces of the object from the measured intensity distribution comprises:
detecting a position of at least one reflected pattern element in the intensity distribution received by the receiving device,
assigning the reflected pattern element to the surface on which the reflection takes place,
using the position of the pattern element on the illumination device and the position of the reflected pattern element in the measured intensity distribution in order to determine the data relating to the surface.

8. The method according to claim 7, wherein, during assigning of the at least one pattern element to the surface on which the reflection takes place, the light intensity of the respective reflected pattern element is compared with a threshold value that is specified or determined from the intensity distribution.

9. The method according to claim 7, wherein during assigning of the at least one pattern element to the surface on which the reflection takes place, the polarization of the respective reflected pattern element is at least approximately determined on the basis of the measured intensity distribution.

10. The method according to claim 1, wherein the irradiated light irradiates planar patterns onto the first and second surface of the object and wherein the determining of the data relating to the surface in the analysis area of one of the two surfaces of the object from the measured intensity distribution comprises
determining the light intensity that is created by reflection at the at least one surface and received by the receiving device, for at least one point in the measured intensity distribution,
assigning the point to the position on the illumination device from which the light originates, which is mapped by reflection at the surface into the point of the measured intensity distribution,
using the position of the point in the measured intensity distribution and the assigned position on the illumination device in order to determine the data relating to the surface.

11. The method according to claim 10, wherein during assigning of the position of the at least one point on the illumination device, the polarization of each reflected point is at least approximately determined on the basis of the measured intensity distribution.

12. The method according to claim 1, wherein for an at least partial suppression or enhancement of the light reflected at the first surface the analysis polarization is mathematically determined, comprising:
breaking down the irradiated polarized light into perpendicular and parallel polarized components in a plane of incidence, multiplying the light intensity of both components by a respective reflection coefficient resulting from an angle of incidence and a refractive index of a material of the object,
combining the components of the reflected light,
determining the polarization direction of the reflected light,
setting the analysis polarization of the analyzer at least approximately perpendicular, or at least approximately parallel, to the polarization direction of the reflected light.

13. The method according to claim 1, wherein for an at least partial suppression or enhancement of the light reflected at the second surface the analysis polarization is mathematically determined, comprising:
breaking down the irradiated polarized light into perpendicular and parallel polarized components in a first plane of incidence of the light on the first surface,
multiplying the light intensity of both components by respective transmission coefficients resulting from a first angle of incidence and a refractive index of the material of the object,
converting said components into perpendicular and parallel polarized components in a second plane of incidence of the reflection at the second surface,
multiplying the light intensity of both components by reflection coefficients resulting from a second angle of incidence and the refractive index of the material of the object and/or of a holder,
converting these components into perpendicular and parallel polarized components in a third plane of incidence of the second refraction at the first surface,
multiplying the light intensity of both components by respective second transmission coefficients resulting from a third angle of incidence and the refractive index of the material of the object,
combining the components of the transmitted light obtained in this way,
determining a polarization direction of the light refracted for a second time at the first surface,
setting the analysis polarization of the analyzer at least approximately perpendicular, or at least approximately parallel, to the polarization direction of the light diffracted for the second time by the first surface.

14. The method according to claim 1, wherein for an at least partial suppression of the light intensity of the light reflected at the first or second surface, the position of the polarizer and/or analyzer is empirically determined, comprising:
setting an arbitrary position of the polarizer and an arbitrary position of the analyzer,
measuring the intensity distribution of the light reflected at the first and at the second surface,
evaluating the contrast between the light reflected at the first surface and the light reflected at the second surface,
iterative adjustment of the positions of the polarizer and/or analyzer, until a predetermined maximum contrast to be achieved between the light reflected at the first surface and the light reflected at the second surface is attained or a limiting value for the intensity of the undesirable light intensity is reached or has a value below the limiting value.

15. A computer program product for determining data relating to a surface of an at least partially transparent object, in particular a spectacle lens, comprising a computer readable storage medium, which contains a program code that is constructed to execute a method according to claim 1, if the program code is executed on a data processing device.

16. An apparatus for determining data relating to a surface of an at least partially transparent object, in particular a spectacle lens, comprising:

at least one illumination device;

a polarizer having an irradiation polarization arranged on an optical axis after or as part of the at least one illumination device;

a holder for the object;

at least one receiving device receiving light that is reflected from the object; and an analyzer having an analysis polarization and being arranged on an optical axis before or as part of the receiving device, wherein an undesirable light intensity reflected by the first or second surface and received by the receiving device is at least partially suppressed through setting of the irradiation polarization of the polarizer or the analysis polarization of the analyzer.

17. The apparatus according to claim 16, wherein discrete pattern elements and/or planar or linear patterns of the illumination device can be irradiated through the polarizer onto the object and can be received by the receiving device through the analyzer.

18. The apparatus according to claim 16, wherein the illumination device with the polarizer irradiates radiation having a predetermined irradiation polarization onto the object, and the receiving device with the analyzer receives a wavefront of a polarization component determined by the analyzer, wherein the irradiated radiation has a predetermined, in particular planar or spherical wavefront and the receiving device analyses the shape of the wavefront and thus operates, in particular, according to the Hartmann principle, the Shack-Hartmann principle, the Moiré principle or by interferometry.

19. The apparatus according to claim 16, comprising a data processing device, wherein the data processing device controls an evaluation of the reflected light radiation received by the receiving device.

20. The apparatus according to claim 19, wherein the data processing device or a further data processing device controls a pattern generation of the illumination device.

\* \* \* \* \*